(12) United States Patent
Baumann et al.

(10) Patent No.: US 9,119,552 B2
(45) Date of Patent: Sep. 1, 2015

(54) APPARATUS AND METHOD FOR ENDOSCOPIC 3D DATA COLLECTION

(71) Applicants: Harald Baumann, Tuttlingen (DE); Klaus M. Irion, Tuttlingen (DE)

(72) Inventors: Harald Baumann, Tuttlingen (DE); Klaus M. Irion, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 364 days.

(21) Appl. No.: 13/687,822

(22) Filed: Nov. 28, 2012

(65) Prior Publication Data

US 2013/0162775 A1 Jun. 27, 2013

(30) Foreign Application Priority Data

Nov. 29, 2011 (DE) .................. 10 2011 119 608

(51) Int. Cl.
*H04N 7/18* (2006.01)
*A61B 1/06* (2006.01)
*A61B 1/05* (2006.01)
*G01S 17/89* (2006.01)
*G02B 23/24* (2006.01)
*G01S 17/02* (2006.01)
(Continued)

(52) U.S. Cl.
CPC ............... *A61B 1/06* (2013.01); *A61B 1/00009* (2013.01); *A61B 1/00096* (2013.01); *A61B 1/05* (2013.01); *A61B 5/065* (2013.01); *G01S 7/4808* (2013.01); *G01S 7/4811* (2013.01); *G01S 17/023* (2013.01); *G01S 17/89* (2013.01); *G02B 23/2415* (2013.01); *A61B 1/00193* (2013.01); *A61B 1/043* (2013.01); *A61B 5/062* (2013.01); *A61B 5/1076* (2013.01); *A61B 2019/5251* (2013.01)

(58) Field of Classification Search
CPC .............. H04N 13/04; H04N 13/0239; H04N 2005/3255; A61B 1/00193; A61B 6/022; G02B 23/2415
USPC .............. 348/45, 65; 600/109, 111, 160, 166; 378/41, 42
See application file for complete search history.

(56) References Cited

U.S. PATENT DOCUMENTS 6,002,423 A * 12/1999 Rappaport et al. .............. 348/42
8,521,331 B2 * 8/2013 Itkowitz ........................ 700/264
(Continued)

FOREIGN PATENT DOCUMENTS

DE 102004008164 B3 10/2005
DE 102006017003 A1 10/2007
(Continued)

OTHER PUBLICATIONS

Holler, et al.; "Spatial orientation in translumenal surgery", in: Minimally Invasive Therapy, vol. 19, 262-273 (2010).

*Primary Examiner* — Victor Kostak
(74) *Attorney, Agent, or Firm* — Whitmyer IP Group LLC

(57) ABSTRACT

Endoscopic 3D data collection, including generating modulated measuring radiation, transmitting the measuring radiation to at least one partial area of a surface of an internal bodily cavity, receiving a signal radiation from the partial area of the surface of the cavity, transmitting the signal radiation from the distal to a proximal end portion of the shaft for reception by a time-of-flight (TOF) image sensor, and a controller to control the generation of the measuring radiation, to control the TOF image sensor and to evaluate the data supplied by the TOF image sensor to generate 3D data, also including a position sensor to record a position and an orientation of the shaft. The invention also relates to a method for endoscopic 3D data collection.

12 Claims, 7 Drawing Sheets

(51) Int. Cl.
*G01S 7/48* (2006.01)
*G01S 7/481* (2006.01)
*A61B 1/00* (2006.01)
*A61B 1/04* (2006.01)
*A61B 5/06* (2006.01)
*A61B 5/107* (2006.01)
*A61B 19/00* (2006.01)

(56) References Cited

U.S. PATENT DOCUMENTS

| | | | | |
|---|---|---|---|---|
| 8,537,203 | B2* | 9/2013 | Seibel et al. | 348/45 |
| 8,734,328 | B2* | 5/2014 | McDowall | 600/109 |
| 8,792,000 | B2* | 7/2014 | Oka et al. | 348/137 |
| 8,831,782 | B2* | 9/2014 | Itkowitz | 700/264 |
| 8,854,426 | B2* | 10/2014 | Pellman et al. | 348/42 |
| 2002/0165448 | A1 | 11/2002 | Ben-Haim et al. | |
| 2006/0025692 | A1 | 2/2006 | Ishihara | |
| 2008/0188716 | A1* | 8/2008 | Heckele et al. | 600/166 |
| 2008/0253511 | A1* | 10/2008 | Boyden et al. | 378/21 |
| 2012/0105612 | A1* | 5/2012 | Yoshino | 348/65 |
| 2014/0018960 | A1* | 1/2014 | Itkowitz | 700/264 |

FOREIGN PATENT DOCUMENTS

| | | |
|---|---|---|
| DE | 102008018636 A1 | 10/2009 |
| DE | 102009013761 A1 | 9/2010 |
| EP | 1746410 A1 | 1/2007 |
| EP | 2108306 A1 | 10/2009 |
| EP | 2260784 A1 | 12/2010 |
| EP | 2551698 A1 | 1/2013 |
| WO | 9403100 A1 | 2/1994 |
| WO | 9829032 A1 | 7/1998 |
| WO | 2005077272 A1 | 8/2005 |

* cited by examiner

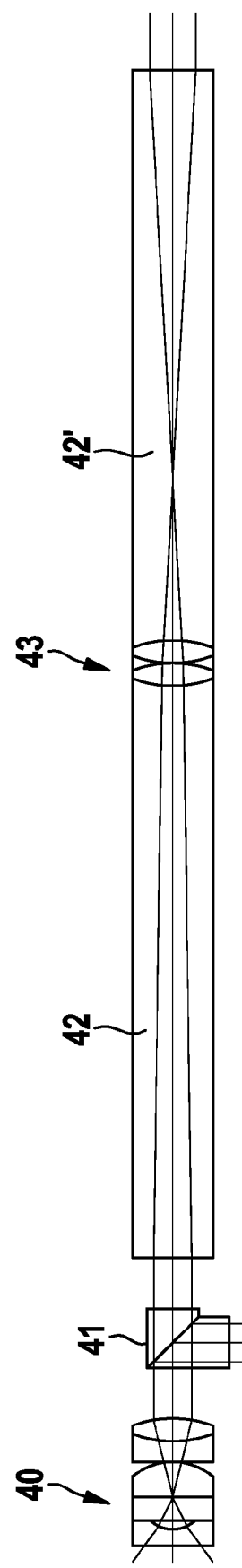
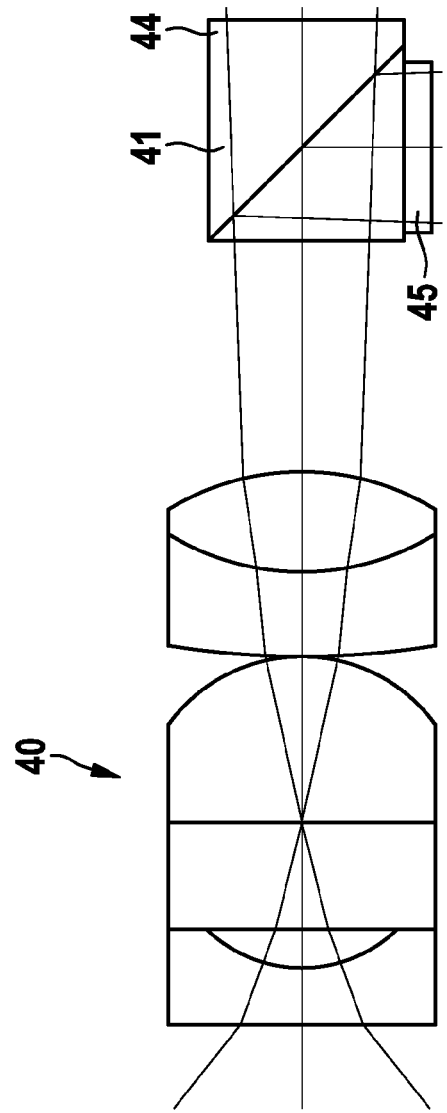
Fig. 2a
Fig. 2b

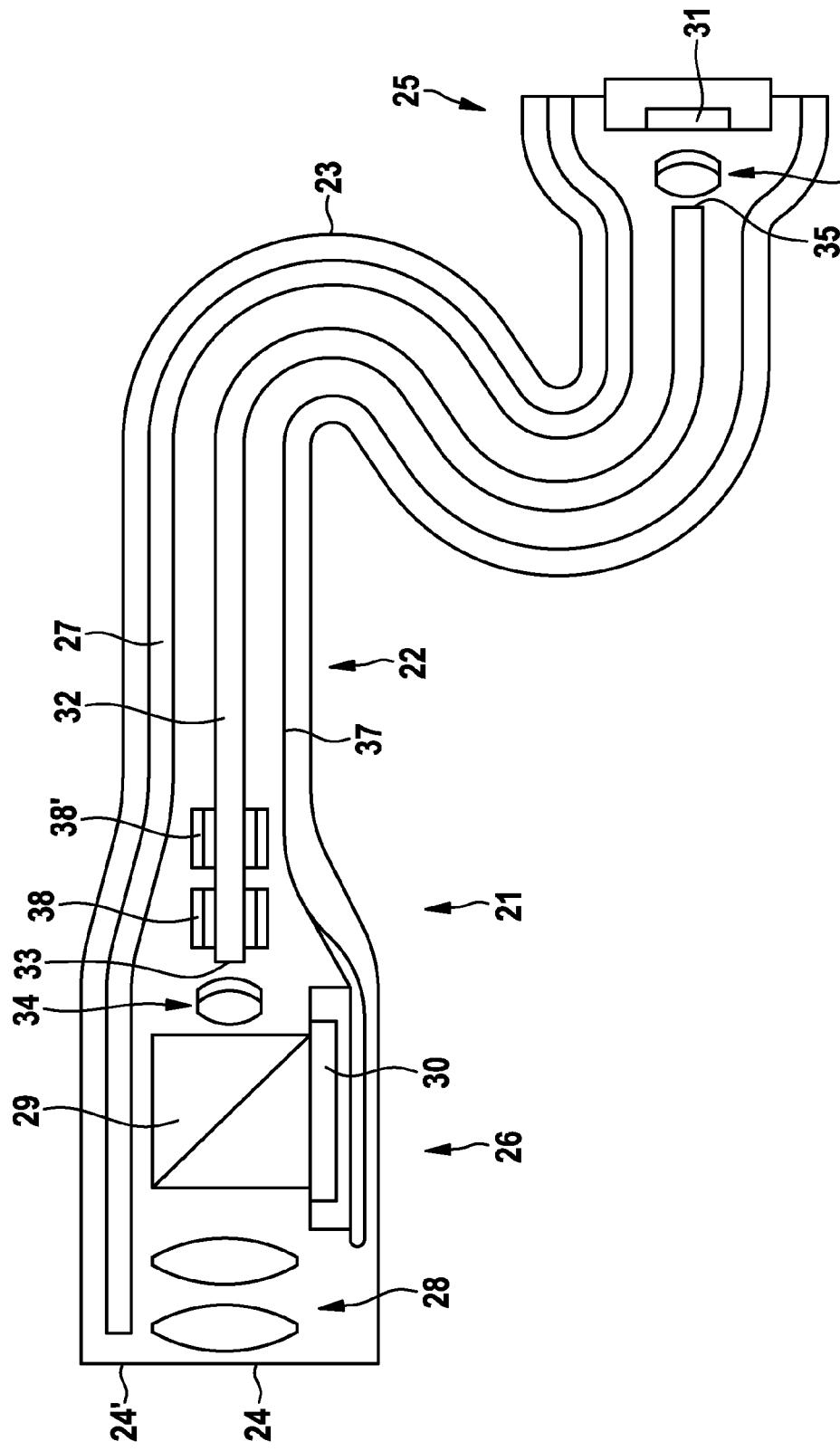

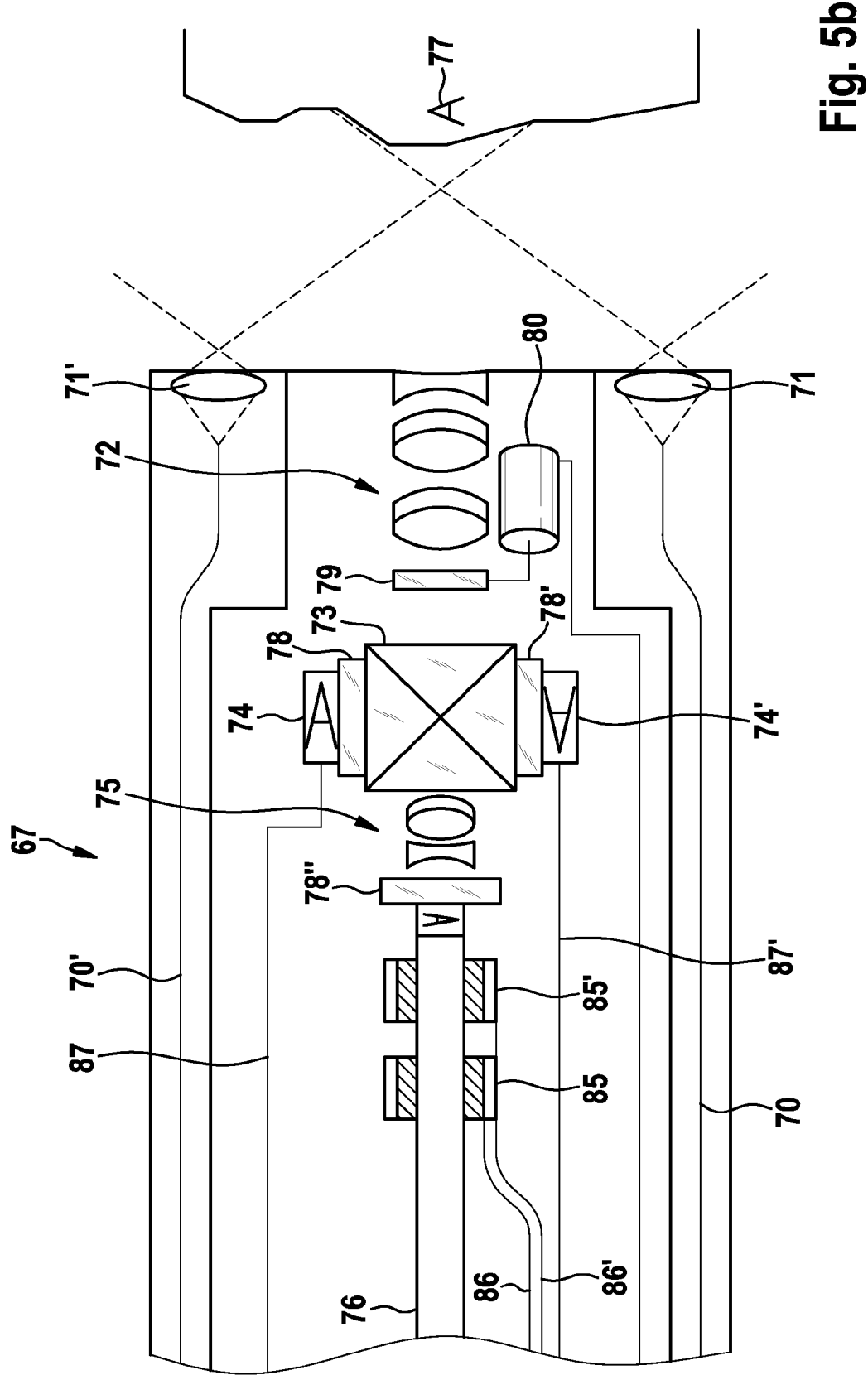

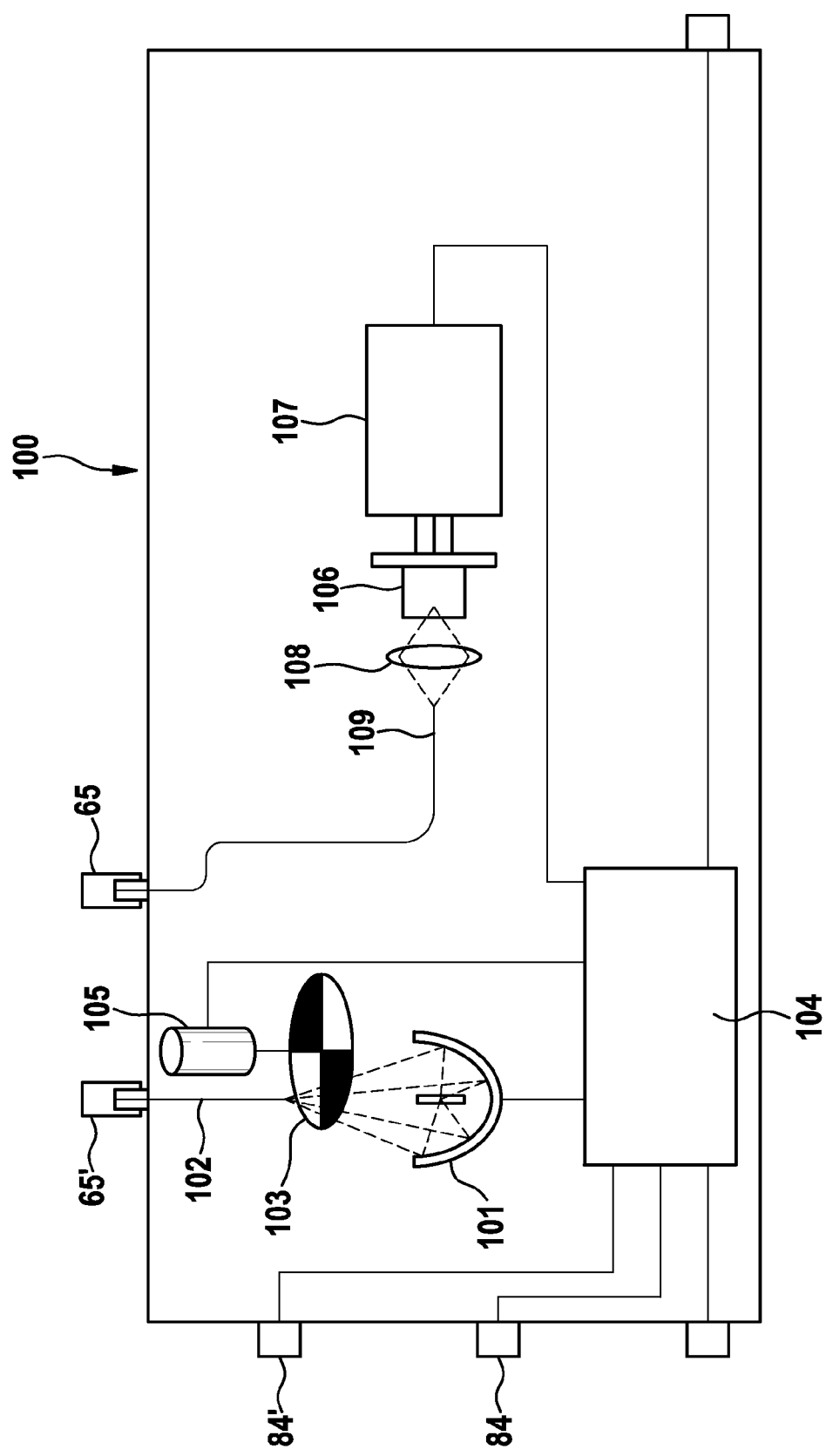

APPARATUS AND METHOD FOR ENDOSCOPIC 3D DATA COLLECTION

FIELD OF THE INVENTION

The present invention relates to an apparatus for endoscopic 3D data collection as well as a corresponding method.

BACKGROUND OF THE INVENTION

Many medical investigations and surgical procedures are performed by endoscopic means today. Consequently the strain on a patient can be considerably reduced. However, because of the reduced visual field as a result of endoscopic access, endoscopic procedures require considerable practice on the part of the operator to make accurate estimates of the distance to a surface of an interior body cavity in which a surgical manipulation is to be performed. For the same reason, the measuring of internal body structures, such as ascertaining the size of a tumor, involves difficulties. Finally, the physician's difficulty in orientation in the interior body cavity, owing to the reduced visual field of an endoscope, can cause portions of the surface of the cavity to be overlooked in an endoscopic investigation, that is, not to be endoscopically collected. Therefore, for endoscopic diagnoses and procedures, the judging of distances and measuring of intracorporeal structures, like the spatial recording or reconstruction of an infernal body cavity, are of great significance. For this purpose, it is essential to collect 3D data on the cavity, and in particular to collect absolute 3D data that are based on an extracorporeal reference coordinate system.

Patent application DE 10 2006 017 003 A1 teaches an endoscope for depth acquisition in which a modulated light signal is emitted and the modulation parameters of the received light signal are used to compute the depth data. Via a plane semi-transparent mirror used as a beam splitter, beams can be received by two image sensors, one of which captures the modulation parameters useful for generating 3D data while the other is provided to capture a visual image of the endoscopic scene, in US 2006/0025692 A1, an endoscopic apparatus for generating an endoscopic fluorescence image is described, such that a distancing signal is generated by a distance-measuring unit, operating for example with ultrasound, microwaves or laser light. It is not possible with the aforementioned solutions to collect absolute 3D data, so that the recorded data are limited to the restricted visual field of the endoscope.

Patent application DE 10 2008 018 636 A1, which is incorporated by reference in the present application, teaches an apparatus for endoscopic 3D data collection, which includes light-generating means for generating at least a modulated measuring radiation, light-transmitting means for transmitting the measuring radiation onto an object to be observed and light-imaging means for imaging a signal radiation from an object to be observed onto a phase-sensitive image sensor. By evaluating the data provided by the phase-sensitive image sensor, 3D data on the observed object are generated. The collection of absolute 3D data is not foreseen by this apparatus.

Patent WO 94/03100 teaches a method for depicting the interior of bodies, where a spatial data field is associated with a body situated in a particularly position and the spatial position of a video camera, before which an endoscope is mounted, is recorded on a continuous basis, in addition, a depiction of a data field, which corresponds in each case to the current viewing angle of the video camera, is computed and the optical image and data field are simultaneously displayed on the monitor. By means of an input process by the user, one or more characteristic points of the data field are harmonized with the associated optical depiction on the screen. For the data field, it is possible to use a three-dimensional reconstruction, which is acquired from one or more previously shot video recordings, with which a distance measurement via ultrasound or by stereometric analysis is associated. The ultrasound distance measurement, however, allows the collection of only relatively few data points, while a stereometric analysis is restricted to high-contrast surfaces. Therefore, and because of the necessary interaction of the user, the usability of the method and the resulting advantages are restricted.

Patent DE 10 2004 08 164 B3, which is incorporated in the present application by reference, discloses an apparatus for producing at least a portion of a virtual 3D model of a bodily interior, said apparatus comprising an endoscope, a positioning system with an inertial sensing system to record the position and orientation of the endoscope, and a distance-measuring system to acquire at least one distance of the endoscope from at least one point on the surface of the bodily interior. Distance is measured with the help of a laser beam emitted by the endoscope on the basis of a triangulation or by run-time measurement of the laser beam or with the help of a pattern projected by the endoscope onto the surface of the bodily interior or else by ultrasound. From points on the surface of the bodily interior recorded by the distance-measuring system, a portion of a virtual model of the surface of the bodily interior is produced. Because this necessitates distance measurement from a number of different positions and orientations of the endoscope, only a relatively low spatial resolution can be achieved.

In an article by Höller et al. "Spatial orientation in translumenal surgery," in *Minimally invasive Therapy* 19 (2010): 282-273, a flexible endoscope is described, on whose proximal end a time-of-flight (TOF) sensor is mounted. An inertial sensor is positioned at the distal end of the endoscope in order to establish the endoscopic image on a gravitational basis or to provide a corrected image horizon. However, an inertial sensor requires a relatively large structural area, and therefore cannot easily be integrated into a distal end portion, especially in flexible endoscopes with small diameter.

SUMMARY OF THE INVENTION

It is the object of the present invention to provide an apparatus for endoscopic 3D data collection, such that the aforementioned disadvantages are avoided as far as possible, it is a particular object of the present invention to provide an apparatus for endoscopic 3D data collection that is simple to operate and has multiple uses, and that allows the collection of three-dimensional data with a high spatial resolution. In addition, the present invention has the object of providing a corresponding method for endoscopic 3D data collection.

Objects of the invention are achieved by an apparatus for endoscopic 3D data collection, comprising a light generator to generate at least a modulated measuring radiation, a light transmitter to transmit the measuring radiation to at least one partial area of a surface of an internal bodily cavity, which is at least partly situated in an endoscopically insertable elongated shaft, an observation lens situated in a distal end portion of the shaft to receive a signal radiation from at least the partial area of the surface of the cavity, an image transmitter situated at least partly inside the shaft to transmit the signal radiation from the distal to a proximal end portion of the shaft for reception by a time-of-flight image sensor and a controller to control the light generator, to control the time-of-flight image sensor, and to evaluate data supplied by the time-offlight image sensor to generate 3D data, characterized in that the apparatus includes a position sensor to capture a position and an orientation of the shaft.

Objects of the invention are achieved by a method for endoscopic 3D data collection, comprising the steps of: generating at least one modulated measuring radiation, transmitting the measuring radiation to at least one partial area of a surface of an infernal bodily cavity by an endoscopically insertable shaft, receiving a signal radiation from at least the partial area of the surface of the cavity using an observation lens situated in a distal end portion of the shaft, transmitting the signal radiation from the distal to a proximal end portion of the shaft using an image transmitter that is situated at least partly inside the shaft, receiving the signal radiation by a time-of-flight image sensor and evaluating the data supplied by the time-of-flight image sensor to generate 3D data, wherein, a position and an orientation of the shaft is recorded using a position sensor for computing absolute 3D data.

An inventive apparatus for endoscopic 3D data collection, in particular for three-dimensional recording of a surface of an internal bodily cavity, includes light-generating means to produce at least one modulated measuring radiation. Here, to generate the measuring radiation, it is possible, for example, to use light-emitting diodes (LEDs), superluminescent diodes, lasers, such as laser diodes or supercontinuum lasers, or other radiation sources that can be modulated in corresponding ways. Laser diodes, in particular, offer the advantage of ease of operation and are cost-effective, compact and easy to modulate. Multimodal laser diodes, as a rule, have higher output capacity than monomodal laser diodes. The measuring radiation can be modulable in sinus shape, possibly above a basal level. For improved operation and more effective cooling, the light-generating means can be situated in their own housing or as a separate light source.

In addition, the inventive apparatus comprises light-transmitting means for conveying the measuring radiation to at least one partial area of the surface of the internal bodily cavity. The light-transmission means here can include, in particular, means for coupling the radiation generated by the light source into a light conductor as well as light conductors to transmit the radiation. Thus, for example, a lens and/or mirror arrangement can be provided for better coupling of the generated radiation, or it is also possible to use fiber-coupled superluminescent or laser diodes, if the light-generating means are situated in their own housing or as a separate light source, a light-conducting cable can be provided to transmit the radiation, where said cable can be provided with connecting means for connecting with the light source or other light conductors.

The light-transmitting means are at least partly positioned in an endoscopically insertable shaft. The shaft is, in particular, elongated and configured with a length and diameter such that it can be inserted into an internal bodily cavity through a natural or artificially produced orifice. The shaft comprises a distal (remote from the user) and a proximal (close to the user) end. The shaft can be configured, in particular, as part of an endoscope including in addition an endoscope head mounted on the proximal end of the shaft, wherein on the endoscope head, for example, a connector is mounted for the light-conducting cable to connect with the light-generating means. The shaft can also be configured as a catheter. The light-transmitting means can include, in particular, an illuminating lens, which is positioned in the endoscopically insertable shaft and by which the measuring radiation is transmitted to the distal end of the shaft to illuminate an area of the cavity that is to be investigated. The illuminating lens can, for instance, be configured as a bundle of optical fibers or as a light-conducting rod. In addition, a widening lens, such as a lens or diffusing screen, can be situated on the distal end of the illuminating lens for uniform distribution of the measuring radiation on the area that is to be examined. To avoid coupling in undesired irradiation, for example to reduce the heat impact in an endoscopic procedure in a live body, filtering means can also be provided to filter out certain portions of the generated radiation in whole or in part.

The inventive apparatus further comprises an observation lens mounted in a distal end portion of the shaft to pick up a signal radiation from at least a partial area of the surface of the cavity. The signal radiation arises, in particular, by reflection and/or scattering of the modulated measuring radiation on the surface of the cavity, but it can also include other portions, such as reflected or scattered white light or fluorescent radiation. The observation lens comprises for this purpose, in particular, a lens arrangement, for example an endoscope objective lens, which generates an image or a first intermediate image of the partial area of the surface of the cavity.

In addition, the inventive apparatus comprises an image transmitter, positioned at least partly inside the shaft, to transmit the signal radiation from the distal to the proximal end portion of the shaft for reception by a time-of-flight (TOF) image sensor. A TOF image sensor is a phase-sensitive image sensor, which is configured in particular as a phase-sensitive drivable solid-state sensor and which includes a number of pixels, which, in pixel-by-pixel form, supply TOF data and thus spatially resolved distance or depth data from measurement points on the surface of the cavity. To generate an image of the partial area of the surface of the internal bodily cavity that is to be investigated on the sensor surface of the TOF image sensor, imaging means such as a lens system can be provided. The observation lens, the image transmitter and/or the imaging means can include filtering means to block off part of the radiation received.

In addition, control and evaluation means are provided to direct the light-generating means to generate the modulated measuring radiation, to direct the TOF image sensor and to evaluate data supplied by the TOF image sensor to generate 3D data of the partial area of the surface of the cavity. In particular, the control means make it possible to generate the modulation of the measuring radiation and a corresponding control of the TOF image sensor for phase-selective reception of the perceived radiation and to read out the signal of the TOF image sensor, which contains phase information in pixel-by-pixel form with reference to the modulation of the signal radiation. From the phase information it is possible to draw conclusions about the time lapse between the occurrence of the signal radiation and the emission of the measuring radiation, so that depth data can be obtained in pixel-by-pixel form. In addition, a display apparatus can be provided to display the recorded distance data or 3D data.

According to the invention, the apparatus further comprises position-sensing means to record a position and an orientation of the shaft. In particular, the position-sensing means are situated inside the shaft or are associated with it in an unequivocal spatial relationship. In particular, the position-sensing means can be configured to interact with a position recording system, so that the position and orientation of the shaft can be determined in relation to an absolute extracorporeal reference coordinate system, especially one independent of the position of the shaft. On the basis of the known association of the position-sensing means with a distal end portion of the shaft, it is possible to draw conclusions from the signals of the position-sensing means about the position and orientation of the distal end portion of the shaft, or of the observation lens situated in it, with respect to the reference coordinate system. The control and evaluation means are configured, in particular, on the basis of data obtained with the help of the position-sensing means from the spatially resolved depth data supplied by the TOF image sensor, to compute 3D data that depict the surface of the internal bodily cavity three-dimensionally with respect to the reference coordinate system.

Thanks to the TOF image sensor, a two-dimensionally resolved collection of the distance or depth data of the surface of the cavity is possible with a high resolution. Because position-sensing means are provided, it is possible to collect data on the position and orientation of the endoscopically insertable shaft that, together with the data supplied by the TOF image sensor, permit absolute coordinates of points on the surface of the cavity to be ascertained. Consequently, in an especially simple way, a 3D collection or spatial reconstruction of at least a portion of a surface of an internal bodily cavity becomes possible, in particular, organ coordinates can be ascertained, which for example allow the measurement of intracorporeal structures, such as the determination of the size of a tumor or measurement of the extent of lesions. As a further consequence, it becomes possible, in especially simple manner, to produce a virtual 3D model of the surface of the internal bodily cavity. These data can be correlated, for example, with 3D surface data, such as have been acquired by CT or MR scanning systems preoperatively.

Thereby, in addition, it becomes easier for a user, such as a surgeon, to be oriented during an endoscopic investigation or an endoscopic operation inside the internal bodily cavity. In natural orifice translumenal endoscopic surgery (NOTES), orientation becomes easier inside the cavity in which the endoscopic access occurs. In extracorporeal lithotripsy, stones can be located endoscopically at a viewing distance and the extracorporeal shock wave source aligned, without in any case requiring the use of x-ray machinery; moreover, the course of the lithotripsy can be monitored endoscopically while maintaining a corresponding viewing distance to protect the endoscope from the effects of the shock waves. Likewise, while using the inventive apparatus, tumor irradiation can be more safely performed, in that the position of the tumor that is to be irradiated is continuously captured and visually controlled and the position of the tumor is reported back to the irradiation device. It also becomes possible to irradiate "nonstable" tumors in easily movable hollow organs, such as in the intestine or in the bladder. In particular with a thin-caliber shaft shape, use in the dental field as well as in vascular endoscopy is possible, such as for a 3D reconstruction of the lumen of a dental root canal as well as for an intraluminal measurement of stenosis.

According to a preferred embodiment of the invention, the shaft is of rigid configuration. In the event that the endoscopically insertable shaft is part of an endoscope, the endoscope can accordingly be configured in the manner of a rigid endoscope. The endoscope shaft can be configured at least partly as a cylindrical tube, in particular a metallic tube. In this case the image transmitter can be made up of one or more relay lens systems situated inside the shaft.

The position-sensing means can be situated at any desired location in the shaft; if the shaft is part of an endoscope, the position-sensing means can also be mounted in or on the head of the endoscope. Because the distance and relative orientation of the distal end portion of the shaft in relation to the position-sensing means are known, it is possible, from the data supplied by a position-recording system concerning the position and orientation of the position-sensing means, to draw conclusions about the position and orientation of the distal end portion of the shaft and thus of the observation lens.

Because, in addition, the radiation run-time from the light-generating device to the distal end portion of the shaft as well as from the observation lens to the TOF image sensor is known, distance data supplied by the TOF image sensor can be converted into absolute coordinates of measurement points on the surface of the cavity, such that the TOF image sensor allows a high spatial resolution.

According to another preferred embodiment of the invention, the shaft is flexible, in the event that the endoscopically insertable shaft is part of an endoscope, the endoscope can accordingly be configured in the manner of a flexible endoscope. A catheter, as well, is understood in the context of the present patent application as a flexible shaft. The flexible endoscope, in particular, can be steerable; that is, the distal end portion of the shaft can be bent at an angle by means of operating elements mounted on the proximal end portion of the endoscope. The shaft can also be semi-rigid, or the endoscope can be configured as a semi-rigid endoscope. With a flexible or semi-rigid shaft, the image transmitter, at least inside the shaft, is configured as a flexible image conductor, which can consist of an ordered glass fiber bundle. The image conductor preferably has a small diameter, preferably less than 1.5 mm, more preferably less than 1.0 mm or even less than 0.6 mm. The image conductor can preferably have a length of more than 150 cm, even more than 300 cm. The image conductor is preferably produced in double-glass technology as a multi-fiber bundle. The position-sensing means in this configuration of the invention are situated in the distal end portion of the shaft. Because of the signal supplied by a position-recording system, the position and orientation of the distal end portion of the shaft can be ascertained in the absolute coordinate system provided by the position-recording system. As a result, with the depth data supplied by the TOF image sensor, absolute coordinates of measurement points on the surface of the intracorporeal cavity can be computed with high spatial resolution.

The position-sensing means preferably include a position sensor by which a position can be ascertained with reference to an extracorporeal reference system. In contrast, for instance, to an inertial sensor, the position sensor makes possible a direct tracking of a position in relation to a reference coordinate system. In contrast, an inertial sensor records an acceleration from which the position is ascertained indirectly by double temporal integration. Inertial position sensors are subject therefore to a time drift, so that the inaccuracy of the ascertained position increases over time. The position-sensing means can advantageously be configured as a position and orientation sensor, which allows a direct recording of a position and of a spatial orientation with respect to a reference system, inertial position sensors, on the contrary, allow as a rule only the direct recording of an alignment of the sensor with respect to a direction indicated by gravity, while, in particular, the orientation in a horizontal plane is determined indirectly by temporal integration, which likewise can result in a time drift. Because the position-sensing means include a non-inertial sensor to ascertain a position or orientation of the endoscope, in particular of the distal end portion of the endoscope shaft, a high degree of precision can be achieved concerning the position and spatial orientation with respect to an extracorporeal reference coordinate system, even in a protracted endoscopic procedure.

The position-sensing means are preferably configured as an electromagnetic position sensor. Such an electromagnetic position sensor interacts, in particular, with a magnetic field generated by an external position-recording system in such a way that makes possible a direct determination—that is, one that does not require double temporal integration—of a position and/or orientation with respect to a reference coordinate system provided by the external position-recording system. The electromagnetic position sensor preferably includes at least two coils on which voltages are induced by an extracorporeal magnetic-field-generating element of the external position-recording system. The electromagnetic position sensor interacts in such a way with the magnetic field generated by the external position-recording system that the position of each of the two coils in relation to the position-recording system can be ascertained from a current or voltage signal supplied by the coils. In this manner, it is possible to determine absolute coordinates—that is, based on the position-recording system—of the electromagnetic position sensor and to ascertain the spatial orientation of the position sensor with sufficient precision, even over the duration of a protracted operation. It is also possible for several position sensors of this type, each with at least two coils, to be present.

According to a preferred embodiment of the invention, the at least two coils of the electromagnetic position sensor surround the image transmitter. In particular, the at least two coils surround the image conductor laterally in a distal end portion of the image conductor, such that the coils preferably are displaced with respect to one another in a longitudinal direction of the shaft. Two coils at a distance from one another in the longitudinal direction can advantageously surround the image conductor coaxially; the coils can be mounted on a metallic carrier or can comprise an iron core. To avoid malfunctioning of the electromagnetic position sensor, the shaft, at least in the area in which the position sensor is situated, is advantageously non-metallic, for example plastic or ceramic, in configuration; this applies as well to the head of a rigid endoscope if the position sensor is situated in it.

In particular, the two coils can be wound about the image conductor inside a rigid shaft or in the distal end portion of a flexible shaft, to make it possible to capture the position and orientation of the distal end portion of the shaft. Consequently, in addition, a compact arrangement is achieved, allowing reception of the position-sensing means in the shaft of the endoscope, in particular in the distal end portion of the shaft, without the diameter of the shaft being significantly enlarged as a result. This permits an especially thin-caliber shaping of the shaft or endoscope.

The external position-recording system preferably includes an extracorporeal magnetic field generator, which, by means of a tetrahedral arrangement of coils, generates a non-homogeneous magnetic field, by which the at least one electromagnetic position sensor can be excited. A magnetic field generator of this type is commercially available from the firm NDI EUROPE GmbH under the trade name AURORA. However, flat-design coil arrangements are also available that are particularly suited to surgical use because of their compact configuration. The external position-recording system further preferably includes an evaluation apparatus, which evaluates the signals generated by the at least one position sensor concerning the position and/or orientation of the position sensor and thus of the shaft in correlation to a spatial reference. The evaluation apparatus makes it possible to process the signals generated by the position sensor into position information, which advantageously can be used in navigating the shaft or an endoscope, for instance in a surgical application.

Alternatively or in addition, at least one position sensor can be provided that is configured as an inertial sensor and makes possible a direct ascertainment of a current position and orientation of the position sensor. In addition, a position recording by means of ultrasound can be provided. With a rigid configuration of the shaft, it is also possible to record the position by an optical tracking system; one example is available from KARL STORZ under the designation SURGICAL COCKPIT® Navigation Panel Unit.

According to an especially preferred configuration of the invention, the TOF image sensor is connected by a flexible image conductor with the proximal end portion of the image transmitter of the shaft or can be detachably connected with it. If the image transmitter inside the shaft is configured with one or more relay lens systems, then the flexible image conductor of the TOF image sensor can be attached to the shaft in such a way that the relay lens system generates an intermediate image on the input surface of the flexible image conductor, if the image transmitter inside the shaft is configured as a flexible image conductor, then an additional flexible image conductor can be attachable on a proximal end surface of the image conductor lead in the shaft; for this purpose an image-conductor coupling can be provided, in the event that the image transmitter inside the shaft is configured as a flexible image conductor, then it can also be configured continuously to the TOF image sensor and can be extended beyond the shaft in the proximal direction. For optimal optical coupling of the TOF image sensor to the image conductor, an imaging lens can be provided that enlarges the image supplied by the image conductor to the format of the TOF image sensor.

Because the TOF image sensor is connected, or can be connected, by a flexible image conductor with the proximal end portion of the image transmitter of the shaft, then despite the space requirement of the TOF image sensors, especially those with high resolution, the shaft can be configured with an especially small diameter; the weight of the TOF image sensor is then non-critical. The shaft or endoscope can be configured as especially handy because the TOF image sensor is not a part of the shaft or endoscope and is not rigidly connected with it. In this way it is possible to achieve an especially high resolution of the 3D data supplied by the TOF image sensor, such that the apparatus or endoscope is still especially easy to operate and especially versatile in its uses, it is important here to consider that TOF sensors frequently operate in the infrared spectral range and the pixel size of sensors of this type is greater as a rule than that of standard image sensors operating in the visual range, in particular, an apparatus or endoscope of this type can be used also in cases in which the diameter of the shaft is restricted for anatomic reasons to a few millimeters or even to less than 1 mm. In addition, the configuration of TOF image sensor that is separate from the shaft or from the endoscope has the advantage that said sensor can be situated at a distance from the patient while the apparatus is in use and therefore is not obliged to meet the same requirements in terms of safety, cleaning and sterilization as the endoscope itself.

It is further preferred that a beam splitter and an additional image sensor to record an additional image of the observed partial area of the surface of the cavity should be situated in the distal end portion of the shaft. While the TOF image sensor as a rule receives an image in the infrared spectral range to ascertain the distance data, the additional image, which is received by the other image sensor, can in particular be a visual image of the partial area of the surface. The distal beam splitter for this purpose is situated in such a way that a part of the signal radiation received by the observation lens is conveyed onto the surface of the additional image sensor, while another part of the signal radiation is coupled info the image transmitter for transmission to the TOF image sensor. The additional image sensor is advantageously of compact configuration so that the diameter of the shaft remains inside the range permissible for insertion into an internal bodily cavity. To supply the additional image sensor as well as to transmit the image data received from if, one or more electrical lines can be situated in the shaft side-by-side to the image transmitter. A more complete recording and display of the observed partial area of the surface of the cavity and the visual acquisition of additional data are made possible by the reception of the additional image.

It is further preferred that an image-processing apparatus should be provided that is adapted in order to associate one item of depth information, which is obtained from the image information of the TOF image sensor, to each of a number of image points, in particular to each image point of the image received by the additional image sensor, if the TOF image sensor has a different resolution than the additional image sensor, then a corresponding interpolation, for example, between neighboring pixels can be performed by means of the image-processing device. The image-processing device can also be configured to smooth the image data of the TOF image sensor, in that for example distance values of pixels, which depart from the mean value of the distance values of each neighboring pixel by more than a threshold value, are replaced by the mean value. As a result, an endoscopy image recorded by the additional image sensor can be linked with the distance data or with an obtained virtual 3D model of the internal bodily cavity and possibly can be displayed with the virtual 3D model on a display unit.

According to an embodiment of the invention, a beam splitter is connected with the proximal end portion of the image transmitter, or can be detachably connected with it, and said beam splitter uncouples a part of the radiation transmitted by the image transmitter. The uncoupled radiation can, in particular, be directed to other image sensors, so that additional image data can be generated. The uncoupled radiation is preferably directed to spectral analysis means, for example for Raman or CARS spectroscopy, so that spectral data can be generated, it is especially advantageous if a distally mounted beam splitter also admits part of the visual spectral range, so that it reaches the proximally positioned beam splitter via the image transmitter and is uncoupled there for spectral analysis. As a result, additional possibilities are opened up for depiction of the endoscopic scene and/or for endoscopic diagnoses.

According to an additional preferred embodiment of the invention, the image transmitter is also configured to transmit a fluorescence excitation radiation to the distal end portion of the shaft, from where the fluorescence excitation radiation is conveyed to the partial area of the surface of the internal bodily cavity. The fluorescence excitation radiation can, for example, be situated in the blue spectral range of the visual spectrum, while the modulated measuring radiation as a rule is in the infrared spectral range. The fluorescence excitation radiation can be coupled into the proximal end portion of the image transmitter directly or via a preferably spectrally selective beam splitter. The beam splitter situated in the distal end portion of the shaft and an additional image sensor positioned there can in this case be configured, in particular, to record the fluorescent radiation, which is emitted from the observed partial area of the surface of the cavity.

An inventive method for endoscopic 3D data collection includes at least the following steps:
  generate at least one modulated measuring radiation,
  transmit the modulated measuring radiation to at least one partial area of a surface of an internal bodily cavity through an endoscopically insertable shaft, which can be, for example, part of an endoscope,
  receive a signal radiation from at least the partial area of the surface of the cavity with the help of an observation lens situated in a distal end portion of the shaft,
  transmit the signal radiation from the distal to a proximal end portion of the shaft with the help of an image transmitter situated at least partly inside the shaft,
  receive the signal radiation through a time-of-flight (TOF) image sensor,
  evaluate the data supplied by the TOF image sensor to generate 3D data of the partial area of the surface of the cavity referring to the observation lens or the distal end portion of the shaft,
  ascertain information on the position and orientation of the shaft with the help of position-sensing means and
  compute absolute 3D data of the partial area of the surface of the cavity on the basis of the 3D data referring to the observation lens or the distal end portion of the shaft and of the information ascertained with the help of the position-sensing means.

It is understood that the aforementioned features and those to be explained hereinafter can be applied not just in the combination indicated each time, but also in other combinations or singly, without departing from the framework of the present invention.

Further aspects of the invention can be seen from the following description of a preferred embodiment and from the appended drawings.

BRIEF DESCRIPTION OF THE DRAWINGS

FIG. 2a shows an observation lens and an image transmitter according to a second embodiment of an inventive apparatus, in schematic depiction.

FIG. 2b shows the observation lens according to the embodiment in FIG. 2a, in enlarged schematic depiction.

FIG. 3 shows an endoscope as part of an inventive apparatus for endoscopic data collection in schematic longitudinal section according to a third embodiment of the invention.

FIG. 5b shows the distal end portion of the endoscope shaft of the apparatus from FIG. 5a, in schematic longitudinal section.

FIG. 5c shows a supply unit of the apparatus from FIG. 5a, in schematic depiction.

DETAILED DESCRIPTION OF THE INVENTION

Figure 1:
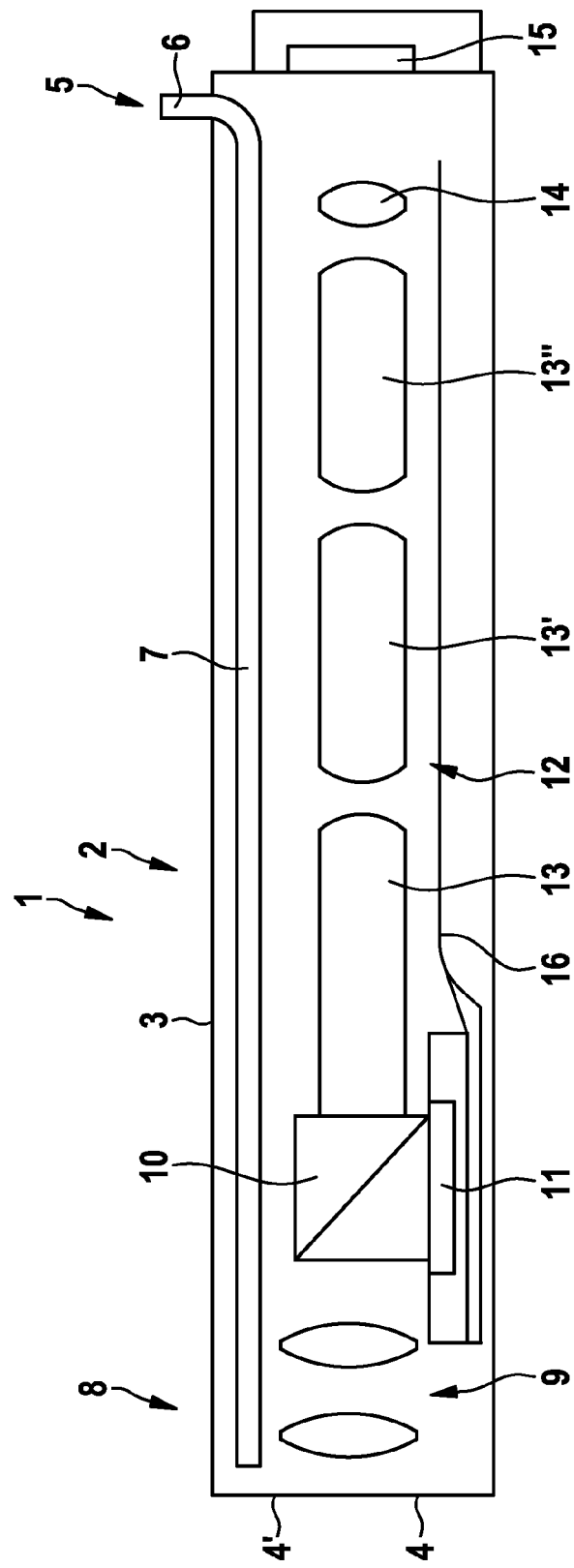
FIG. 1 shows an endoscope as part of an inventive apparatus for endoscopic data collection in the schematic longitudinal section according to a first embodiment of the invention.

As shown schematically in FIG. 1, an endoscope 1, according to an embodiment of the invention, includes an elongated rigid shaft 2, which is made up of a cylindrical tube 3, which comprises one or more distal windows 4, 4' and in which additional optical, mechanical and electronic components are placed. Situated in the proximal end portion 5 of the shaft, which is configured as an endoscope head, is a light connector socket 6, to which a light-conducting cable can be coupled for connection with a non-illustrated light source. The light source generates both a modulated measuring radiation for distance measurement and an illuminating light for visual observation of a surface area of an internal bodily cavity. The measuring radiation and illuminating light are designated here as "light", regardless of whether visible light or infrared or ultraviolet radiation are meant. A light conductor 7, which for example can consist of a fiber glass bundle, is situated inside the shaft 2 to transmit the coupled-in light to the distal end portion 8 of the endoscope; a number of light conductors can also be provided. At the distal end of the light conductor 7, a widening lens (not illustrated) can be provided for uniform illumination of an area that is to be observed. The light transmitted by the light conductor 7 emerges through the window 4' in the direction toward the area of the cavity that is to be observed.

From the observed area of the surface of the cavity, a signal radiation enters through the window 4, which can be configured as a single unit with the window 4', info the observation lens of the endoscope 1, said lens being configured in particular as an endoscope objective lens 9. The signal radiation includes a portion that is generated by the measuring radiation through reflection by the surface of the cavity and/or by scattering. In addition, the visual illumination light reflected by the surface, as well as in some cases fluorescent light, enters the observation lens. A beam splitter 10, mounted downstream from the endoscope lens 9 in the observation light path, deflects a portion of the received light transverse to the longitudinal direction of the shaft 2 to an image sensor 11 mounted in the distal end portion 8 of the endoscope 1. The optical axis of the image sensor 11 is aligned approximately perpendicular to the shaft longitudinal direction; that is, the surface of the image sensor 11 is situated in the shaft longitudinal direction. An additional portion of the received light, which contains at least a portion of the signal radiation, for example a near-infrared portion, is admitted by the beam splitter 10 in the longitudinal direction of the shaft 2 to an image transmitter 12, which includes rod lenses 13, 13', 13" or relay lens systems composed of them. The light path is telecentric at the image end, to achieve the most efficient coupling possible into the rod lens 13. In addition, the aperture of the ray bundle generated by the objective lens 9 is adjusted to the aperture of the rod lenses 13, 13', 13" in order to fill them as much as possible. The image generated by the objective lens 9, which is in particular a retrofocus objective lens, is situated on the proximal outlet surface of the beam splitter 10, and likewise on the lateral outlet surface facing the image sensor 11, or at least close to these outlet surfaces. On the proximal outlet surface of the beam splitter 10, the rod lens 13 is preferably attached with a cement whose refractive index is equal to that of the rod lens 13 or in any case smaller than the larger of the refractive indexes of the beam splitter 10 and rod lens 13.

An image of the surface of the cavity is generated through an imaging lens 14 onto a surface of a TOF image sensor 15. The beam splitter 10 can, for example, be configured spectrally selectively in such a way that light in the visual range is deflected onto the image sensor 11 to receive a visual image of the observed area, while in the infrared range the signal radiation is passed through the beam splitter 10 and reaches the TOF image sensor 15 to generate spatially resolved distance data, if the measuring radiation is also situated in the visual spectral range, then on the other hand a non-spectrally selective configuration of the beam splitter 10 is advantageous.

To supply the distal image sensor 11 as well as for data transmission to the non-illustrated control and evaluation device, an electric line 16 is provided that is likewise situated inside the shaft 2. It can end in the proximal end portion 5 of the shaft 2 in a plug for connecting a corresponding cable, or can end with corresponding lines of the TOF image sensor 15 in a common plug or can be lead in a common cable (not illustrated). The endoscope 1 includes, in addition, position-sensing means, in particular two coils that surround the image transmitter in a compact arrangement (not shown). Because of the rigid configuration of the shaft 2, by ascertaining the position and orientation of the position-sensing means, if is possible to ascertain the position and orientation of the distal end portion 8 of the shaft 2, in particular of the endoscope objective lens 9 as well as of the images, generated by it, of the observed portion of the surface of the cavity. Consequently, absolute 3D data, based on a coordinate system independent of the endoscope 1, can be computed by the control and evaluation device on the basis of the 3D data recorded by the TOF image sensor 3l.

In the embodiment shown in FIG. 1, the TOF image sensor 15 can be connected with the proximal end of the endoscopic shaft 2 or can be received in a proximal end portion 5 of the shaft 2, configured as an endoscope head. In a non-illustrated embodiment, the TOF image sensor can be connected by a flexible image conductor with the proximal end of the shaft 2. Handling of the endoscope 1 is hereby substantially facilitated, especially when the TOF image sensor has a higher resolution and accordingly demands more space. The visual image sensor 11, on the other hand, can be sufficiently compact in configuration to be incorporated in the distal end portion 8 of the shaft 2 without causing a substantial enlargement of the diameter of the shaft 2; the electric line 16 also causes no enlargement of the shaft diameter.

An observation lens and an image transmitter according to an additional embodiment of an inventive apparatus are shown schematically in FIG. 2a. The observation lens includes an endoscope objective lens 40, which consists of several lens groups. The light path is telecentric at the image end. Situated in the observation light path downstream from the endoscope objective lens 40 is a beam splitter 41, which is followed in the proximal direction by a relay lens system 43 composed of rod lenses 42, 42'. The endoscope objective lens 40 and the beam splitter 41 are shown in FIG. 2b in enlarged depiction. As can be recognized in FIG. 2b, the beam splitter 41 can comprise an extension 44 with respect to the cubical shape in the axial direction, along with a plane-parallel plate 45 that is cemented onto it in the transverse direction. As a result of the plane-parallel plate 45, the optical path lengths of the two optical paths inside the beam splitter are equal or at least nearly equal. Consequently, the imaging quality is improved, and in addition both images are of equal size. In the other described embodiments of the invention as well, the optical path lengths of the two paths in the beam splitter are ideally equal. The arrangement shown in FIGS. 2a and 2b can be inserted into a rigid shaft according to FIG. 1.

As shown in FIG. 3, an endoscope 21, according to an additional embodiment of the invention, includes an elongated flexible shaft 22. The shaft 22 includes a flexible outer shaft 23, which is concluded in its distal end portion by one or more distal windows 24, 24'. Additional optical, mechanical and electronic components are enclosed inside the flexible outer shaft. Situated in the proximal end portion of the shaft is an endoscope head 25, which for example can include control elements to control the endoscope tip, that is, the distal end portion 26, as well as irrigation and suction connectors (not illustrated). In addition, a light-conducting cable to connect with a light source as well as electrical supply and signal cables can also be coupled on the endoscope head 25 (not illustrated).

As already described in relation to FIG. 1, the measuring radiation and illumination light are guided through a light conductor 27 to the distal end portion 26 of the endoscope 21 and, in some cases, conducted via a non-illustrated widening lens through the window 24' to a surface area of an internal bodily cavity. The light conductor 27 consists of a glass fiber bundle and is of flexible configuration.

As also explained above with respect to FIG. 1, the signal radiation enters from the observed area of the surface of the cavity through the window 4 into the endoscope objective lens 28 and is divided by the beam splitter 29 into a portion that arrives at an image sensor 30 situated in the distal end portion 26 in the longitudinal direction of the shaft 22, and another portion that is transmitted to a TOF image sensor 31 situated in the endoscope head 25. To transmit the corresponding portion of the signal radiation to the TOF image sensor 31, inside the shaft 22 a flexible image conductor 32 is situated consisting of an ordered bundle of optic fibers. On the distal end surface 33 of the image conductor 32, the portion of the signal radiation is imaged by an adaptive lens 34. The numerical aperture is adjusted by the adaptive lens 34 in order to allow optimal use of the optic fibers. According to a non-illustrated embodiment, the image conductor 32 can be cemented onto the proximal-end outlet surface of the beam splitter 29, wherein the cement preferably has a refractive index that is equal to that of the fiber core or between that of the fiber core and that of the beam splitter 29. From the proximal end surface 35 of the image conductor 32, an image is generated by an imaging lens 36 onto the sensor surface of the TOF image sensor 31. An electric line 37, likewise mounted inside the shaft 22, serves to supply the distal image sensor 30 and for data transmission. Light-conducting cables and electric cables to connect the light conductor 27 or the line 37, as well as to connect the TOF image sensor 31 with a non-illustrated control and evaluation device, can be connected to the endoscope head 25.

Coils 38, 38' of an otherwise non-illustrated position-sensing or position-recording system are situated in the distal end portion 26. The coils 38, 38' surround the image conductor 32 in its distal end portion; the coils 38, 38' in this manner can be situated inside the shaft 22, without it being substantially enlarged in diameter. At least in the area of the coils 38, 38', the outer shaft 23 as well as, in some cases, other surroundings and reinforcements are of non-metallic construction, so as not to disturb the functioning of the position-sensing system. From the coils 38, 38', non-illustrated electric lines are lead inside the shaft 21 to the endoscope head 25 and likewise cause no enlargement of the shaft diameter. Because the coils 38, 38' are situated in the distal end portion 26 of the shaft 22, the coils stand in a fixed geometric relationship to the distal end of the shaft, in particular to the endoscope objective lens 28, to the image generated by it on the distal image sensor 30, and to the image generated by the endoscope objective lens 28 via the adaptive lens 34 on the distal end surface 33 of the image conductor 32. As a result, capturing of the position and orientation of the distal end portion 28 of the shaft 22 is possible and thereby a conversion of 3D data collected by the TOF image sensor 31 into absolute 3D data based on the reference coordinate system of the position-recording system.

Figure 4:
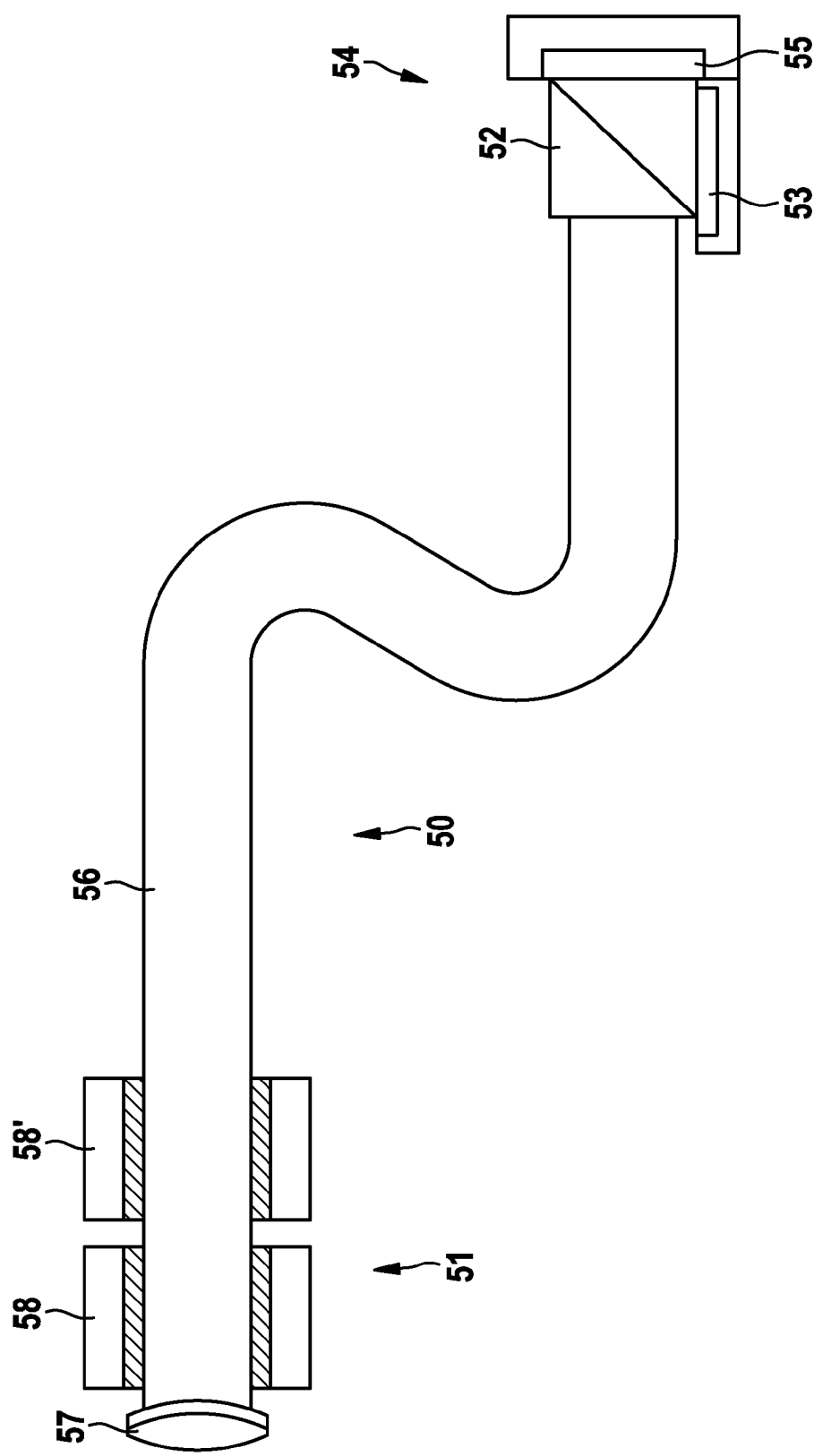
FIG. 4 shows an endoscope as part of an inventive apparatus for endoscopic data collection in schematic longitudinal section according to a fourth embodiment of the invention.

FIG. 4 shows in simplified schematic depiction an additional embodiment of a flexible endoscope 50 as part of an inventive apparatus. The embodiment shown in FIG. 4 is distinguished from that shown in FIG. 3 in that a beam splitter 52 and an image sensor 53 are not situated in the distal end portion 51 but rather in the proximal end portion 54 of the endoscope 50. A TOF image sensor 55 is also situated in the proximal end portion 54. The beam splitter can, for example, deflect a portion of the signal radiation to generate a visual image of an area of the internal bodily cavity onto the image sensor 53 and can pass the portion of the signal radiation used to generate the 3D data onto the TOF image sensor 55; the arrangement of the image sensor 53 and of the TOF image sensor 55 can also be reversed.

Inside a flexible shaft, not shown in FIG. 4, a flexible image conductor 56 is situated into which the signal radiation from the observed area is coupled by a symbolically indicated endoscope objective lens 57. Images of the observed area are generated onto the sensor surfaces of the image sensor 53 as well as of the TOF image sensor 55 by an imaging lens that is situated in the proximal end portion 54 of the endoscope 50 and not illustrated, as well as, in some cases, an adaptive lens.

Situated in the distal end portion 51 of the endoscope 50 are two coils 58, 58' of a position-recording system, whose windings surround the image conductor 58 in a compact arrangement. As explained with reference to FIG. 3, with the data supplied by the position-recording system, it is possible to generate absolute 3D data about the surface of the observed cavity.

With additional, non-illustrated embodiments of the inventive apparatus, which otherwise are configured as is shown in FIG. 3 or FIG. 4, the TOF image sensor can be connected via a flexible image conductor with the proximal end of the shaft. Consequently, operation of the endoscope is substantially facilitated.

Figure 5A:
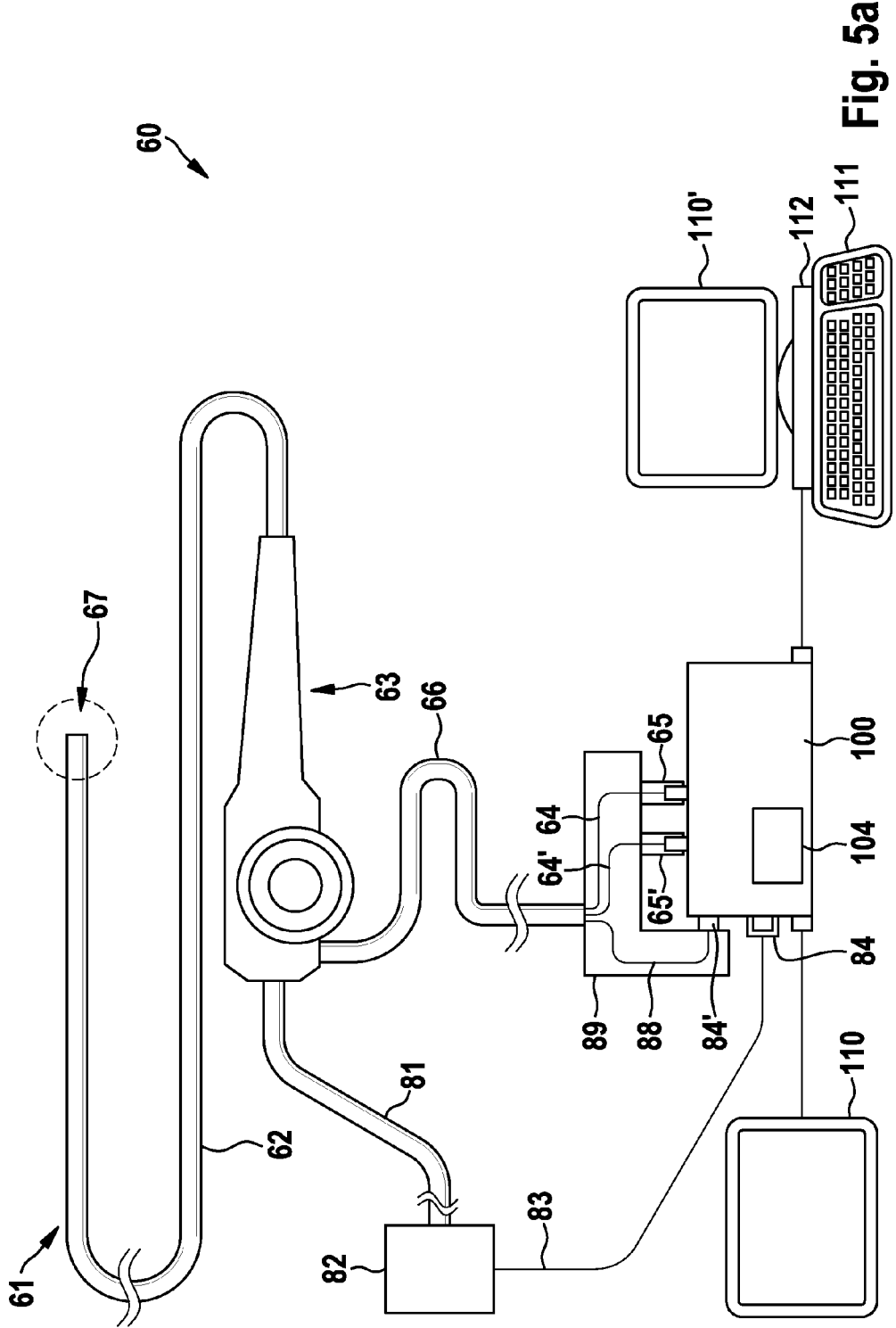
FIG. 5a shows an inventive apparatus according to a fifth embodiment of the invention, in schematic depiction.

As shown in FIG. 5a, an inventive apparatus 60 according to an additional embodiment includes an endoscope 61, a supply unit 100 as well as display and input devices, such as image screens 110, 110' and a keyboard 111. The endoscope includes a flexible shaft 62 and an endoscope head 63. The supply unit 100 includes light sources to generate a modulated measuring radiation, for example in sinus shape, and a white light illumination. To transmit both types of radiation, in each case light-conducting cables 64, 64' are provided that can be connected with the supply unit 100 via connectors 65, 65' and with the endoscope 61 via a supply cable 66. Both types of radiation can also be transmitted by a common light conductor; it is also possible to provide separate light cables in each case. The supply cable 66 can be detachably connected with the endoscope head 63, for which purpose a corresponding coupling can be provided (not illustrated).

The distal end portion 67 of the endoscope 61, that is, the endoscope tip, is shown enlarged in FIG. 5b. The measuring radiation and the white light are guided by the endoscope light conductors 70, 70' to the distal end of the endoscope. The widening lenses 71, 71' situated there serve to uniformly distribute the illumination radiation onto a partial area of the surface of an internal bodily cavity, such as a tissue area in the cavity. The distal end portion 67 contains an endoscope objective lens 72 to generate an image of the tissue area, a beam splitter configured as a beam splitter cube 73 to distribute the image, one or more image sensors 74, 74' as well as, in some cases, one or more adaptive lenses 75, shown here by way of example with the image conductor 76. The adaptive lens 75 is configured in such a way that the same field of view is imaged on the distal end surface of the image conductor 76, despite a different size, as on the image sensors 74, 74'. This is illustrated symbolically in FIG. 5b by the imaged structure 77, which is imaged by the adaptive lens configured as a reducing lens onto the end surface of the ordered fiber bundle of the image conductor 76 as smaller than on the image sensors 74, 74'. In addition, preparation lenses can be present that, for example, can be configured as filters 78, 78', 78", such as color filters, electronically adjustable filters, prisms, lengthening plates or spatial frequency filters (anti-aliasing filters), in addition, a filter 79 that can pivot in and out can be provided with an actuator 80.

The image generated by the endoscope objective lens 72 on the distal end surface of the image conductor 76 is conducted by the image conductor 76 to the endoscope head 63 and by the image conductor 81 coupled there to a TOF camera unit 82, which contains a TOF image sensor as well as an imaging lens to generate an image on the sensor surface of the TOF image sensor (see FIG. 5a). The image conductor 76 can also be configured as a single unit with the image conductor 81, so that a light loss at the coupling site can be avoided, if a rigid endoscope is used instead of the illustrated flexible endoscope 61, then the generated image can also be transmitted by relay lens systems to the endoscope head. The TOF camera unit 82 can be connected by an electric cable 83 and the connector 84 to the supply unit 100.

As indicated symbolically in FIG. 5b, two coils 85, 85', whose windings surround the image conductor 76, are situated on the image conductor 76 in its distal end portion, displaced in the longitudinal direction of the distal end portion 67. Said coils 85, 85' constitute the sensing means of a non-illustrated electromagnetic position-recording system. The position-recording system generates an external magnetic field configured in such a way that the position of the coils 85, 85' inside the magnetic field, that is, in relation to an outer coordinate system that is independent of the position of the endoscope 61, can be ascertained from the current or voltage signals supplied by the coils 85, 85'. The orientation of the distal end portion 67 of the shaft 62 and thus the viewing angle can be ascertained from the difference between the signals of the two coils 85, 85'. The signals of the coils 85, 85' are transmitted to the endoscope head 63 by electric lines 86, 86'. The other lines 87, 87' serve for supply and signal transmission of the image sensors 74, 74', wherein electronic components to control the image sensors 74, 74' can be situated in the distal end portion 67 or in the endoscope head 63. The coils 85, 85' and the image sensors 74, 74' as well as, in some cases, additional electric devices of the endoscope 61 are connected with the supply unit 100 by the line 88 symbolically depicted in FIG. 5a and the connector 84'. The light conductors 64, 64' and the line 88 can be combined in a connection box 89.

The supply unit 100 is schematically illustrated in FIG. 5c. To generate a white light illumination, the supply unit contains a metal halide arc discharge lamp 101, which can include a reflector, as well as additional elements for collimation or coupling into a light conductor 102. Alternatively, LED, xenon or halogen lamps can also be used as white light source, as can RGB or supercontinuum laser sources, in addition, a heat protection filter can be provided (not illustrated). To prevent white light from disturbing the depth measurement, a chopper wheel 103 is provided that interrupts the light flow as soon as a distance data collection occurs. This can be entered manually in order to observe alternatively in white light and in measuring light or else to record a fluorescence image. However, it is also possible to switch automatically, in particular within a video frequency or a fraction thereof, between white light and fluorescence observation and 3D measurement. The control device 104 controls the power drive 105 of the chopper wheel corresponding to the particular requirements, for example synchronously with reading out the respective image sensor, instead of a chopper wheel, an oscillating mirror or an electronically controlled filter can be used. In using solid-state light sources, such as LED or laser light sources, they can be controlled directly in the corresponding frequency. The light conductor 102 introduces the light into the light conductor 64' via a connector 65'.

To generate the measuring radiation, a laser diode 106 is provided, which is powered by an electronic driver 107 and whose light is coupled into a light conductor 109 via a collimation lens 108. Alternatively, a fiber-coupled light-emitting diode or a superluminescent diode can be employed. In addition, means can be provided to reduce the coherence of the measuring radiation. The generated light is introduced into the light conductor 64 via a connector 65 for transmission into the endoscope 61 (see FIG. 5a). The laser diode is modulated synchronously by the control device 104 to read out the phase-sensitive image sensor.

The white light and the measuring radiation can also be coupled into a common light conductor. In addition, fluorescence excitation light, which can be generated by the light source 101, for example via a beam splitter mounted in the endoscope head or in an integrated supply unit containing the TOF camera unit 82, can be coupled into the image conductor 81 and by it can be conducted to the distal end portion 67 of the endoscope 61 (not illustrated).

The control device 104 also serves to control the TOF camera unit 82 and to evaluate signals supplied by it or by the TOF image sensor. The TOF image sensor registers, in pixel-by-pixel form, the intensity of the received signal radiation and the phase shift, that is, the time delay between the emitted measuring radiation and the recorded signal radiation. By means of an evaluation, as indicated for example in EP 1 746 410 A1, the phase shift and thus the time delay corresponding to the time of flight can be ascertained. From the time delay it is possible to reconstruct 3D data that refer to the end portion 67 of the endoscope 61, that is, are relative 3D data.

In addition, the image sensors 74, 74' are also connected with the control device 104, which reads out image signals or processes them for a display, controls the chopper wheel 103 and the laser diode 106, accordingly, synchronously and transmits the image data on to a computer 112 for further processing, display and storage. Moreover, the control device 104 is configured to process signals from the coils 85, 85' or to communicate with the position-recording system. Position data thus obtained make it possible to determine the position and orientation of the distal end portion 67 of the endoscope 61 in relation to an extracorporeal coordinate system provided by the position-recording system. From these and from the relative 3D data ascertained from the signals of the TOF image sensor, the control device 104 ascertains 3D data of the observed partial area of the surface of the internal bodily cavity that are absolute, that is, based on the extracorporeal coordinate system. These data are transmitted to the computer 112.

By linking 3D data, which have been acquired at different positions and orientations of the endoscope 61 or of its distal end portion 67, a practically complete recording of the inner surface of the cavity is possible, as well as the establishment of a virtual 3D model of the internal bodily cavity. The generated absolute 3D data can also be evaluated for measurement of length, surface or volume, in addition, in the control device 104 or in the computer 112, a possibility of linking or synoptic depiction of the various image data supplied by the TOF image sensor as well as by the image sensors 74, 74' is provided, along with, in some cases, the generation of a synthetic stereo image. The image data can be depicted on the screens 110, 110'. In addition, an input device is available for entering instructions of a user, for example a keyboard 111, a touch screen or else a speech recognition device.

A TOF camera unit 82 and/or a supply unit 100, as described above, can also be used in conjunction with endoscopes, which are configured according to FIGS. 1 through 4. Here, as well as in the embodiment according to FIGS. 5a through 5c, the TOF camera unit can also be integrated into the supply unit 100. In this case the image conductor 81 preferably runs in the supply cable 66 and can be introduced via a plug-in system into the supply unit 100 (not illustrated). The result is an especially compact and easily operated apparatus. The arrangement made up of the beam splitter 52, image sensor 53 and TOF image sensor 55 in the embodiment according to FIG. 4 can also be integrated into the supply unit and connected with the endoscope 50 via an image conductor that is preferably lead through a supply cable.

For the use of an inventive method for endoscopic 3D data collection, the endoscope 1, 21, 50, 61 is introduced into the bodily cavity in which the investigation or procedure is to take place. The TOF image sensor, provided it does not form a unit with the endoscope or is not already connected with it, is connected to the endoscope 1, 21, 50, 61, for example via an image conductor 81 and a corresponding coupling. If the light-generating means are not a part of the endoscope, then a light source or the supply unit 100, which contains light-generating means to generate a measuring radiation, is connected with the endoscope 1, 21, 50, 61 via a light cable or the supply cable 66. A fastening of the endoscope 1, 21, 50, 61 to a retainer, which prevents movement of the endoscope in relation to the examined patient or to the cavity during the procedure, is not necessary as a rule because of the collection of absolute 3D data.

To execute the inventive method for 3D data collection, illumination light, in particular the measuring radiation and white light, is generated in the supply unit 100. The measuring radiation is intensity-modulated in sinus shape with a frequency of, for example, approximately 10 to 100 MHz. The white light can include, for example, the entire visible spectrum or part of it, but it can also consist of one or more narrow-band portions. The white light is advantageously switched in video frequency.

White light and measuring radiation are conducted by light conductor 7, 26, 70, 70' to the area to be observed. An image is generated on the TOF image sensor 15, 31, 75 by the observation lens 9, 28, 57, 72 and the image transmitter 12 or image conductor 32, 56, 76, 81. By a read-out from the image sensor synchronized with the modulation of the measuring radiation, phase-dependent data are acquired in pixel-by-pixel form that are processed to intensity and phase information by the control device 104. The control device 104 thereby generates depth information, which corresponds to the time delay of the signal radiation in relation to the measuring radiation, and 3D data therefrom. The signal of the TOF image sensor can also be used to generate a fluorescence image; in addition, by the other image sensors 11, 30 74, 74' additional images can be generated.

The signals of the position-sensing means, in particular of the coils 38, 38', 58, 58', 85, 85', are further captured by the control device and used to generate absolute 3D data. The 3D data as well as, in some cases, the other images, can be depicted for the user on appropriate display devices 110, 110' and can be available for further image-processing steps or for storage. Thus, an RGB or fluorescence image, for instance, can be depicted in alternation or superimposed with the 3D data.

Provided that no 3D data processing is desired, operation without a TOF sensor can also be foreseen, such that for example the image conductor 81 is not connected with the endoscope 81. Here, as with a standard video endoscope for example, only a visual image of a partial area of the internal bodily cavity can be generated.

What is claimed is:

1. An apparatus for endoscopic 3D data collection, comprising
a light generator to generate at least a modulated measuring radiation,
a light transmitter to transmit the measuring radiation to at least one partial area of a surface of an internal bodily cavity, which is at least partly situated in an endoscopically insertable elongated shaft,
an observation lens situated in a distal end portion of the shaft to receive a signal radiation from at least the partial area of the surface of the cavity,
an image transmitter situated at least partly inside the shaft to transmit the signal radiation from the distal to a proximal end portion of the shaft for reception by a time-of-flight image sensor, and
a controller to control the light generator, to control the time-of-flight image sensor, and to evaluate data supplied by the time-of-flight image sensor to generate 3D data,
characterized in that the apparatus includes a position sensor to capture a position and an orientation of the shaft.

2. The apparatus according to claim 1, wherein the shaft is of rigid configuration.

3. The apparatus according to claim 1, wherein the shaft is of flexible configuration, the image transmitter is a flexible image conductor and the position sensor is situated in the distal end portion of the shaft.

4. The apparatus according to claim 1, wherein the position sensor, comprises a position and orientation sensor.

5. The apparatus according to claim 1, wherein the position sensor is configured as an electromagnetic position sensor, which comprises at least two coils.

6. The apparatus according to claim 5, wherein the coils surround the image transmitter.

7. The apparatus according to claim 1, wherein the time-of-flight image sensor is connectible with the proximal end portion of the image transmitter by a flexible image conductor.

8. The apparatus according to claim 1, wherein in the distal end portion of the shaft a distal beam splitter and an additional image sensor are situated to collect an additional image of the partial area of the surface of the cavity.

9. The apparatus according to claim 8, wherein the apparatus includes an image-processing device, which is configured to associate depth information acquired from data supplied by the time-of-flight image sensor, with image points of the additional image.

10. The apparatus according to claim 1, wherein a proximal beam splitter, coupleable to a spectral analyzer, is connectible with the proximal end portion of the image transmitter.

11. The apparatus according to claim 1, wherein the image transmitter is configured to transmit a fluorescence excitation radiation from the proximal to the distal end portion of the shaft.

12. A method for endoscopic 3D data collection, comprising the steps of:
generating at least one modulated measuring radiation,
transmitting the measuring radiation to at least one partial area of a surface of an internal bodily cavity by an endoscopically insertable shaft,
receiving a signal radiation from at least the partial area of the surface of the cavity using an observation lens situated in a distal end portion of the shaft,
transmitting the signal radiation from the distal to a proximal end portion of the shaft using an image transmitter that is situated at least partly inside the shaft,
receiving the signal radiation by a time-of-flight image sensor and evaluating the data supplied by the time-of-flight image sensor to generate 3D data, and
recording a position and an orientation of the shaft using a position sensor for computing absolute 3D data.

* * * * *